United States Patent [19]

Snyder et al.

[11] Patent Number: 5,001,056
[45] Date of Patent: Mar. 19, 1991

[54] PREPARATION OF MONOCLONAL ANTIBODIES

[75] Inventors: Solomon H. Snyder, Baltimore, Md.; Mathew M. S. Lo, London, United Kingdom; Tian Y. Tsong, Baltimore, Md.; Mary K. Conrad, Scottdale, Pa.

[73] Assignee: The Johns Hopkins University, Baltimore, Md.

[21] Appl. No.: 618,946

[22] Filed: Jun. 8, 1984

[51] Int. Cl.[5] .................. C12N 15/00; C12P 21/00 C12N 5/02, 13/00
[52] U.S. Cl. .................................................. 435/68
[58] Field of Search .................. 435/68, 172.2, 173, 435/240, 241, 948; 424/85; 436/548; 935/93, 100, 104, 54

[56] References Cited

U.S. PATENT DOCUMENTS 4,271,145  6/1981  Wands et al. .................. 435/948

FOREIGN PATENT DOCUMENTS 0028902  5/1981  European Pat. Off. .............. 935/93

OTHER PUBLICATIONS

Bankert et al., "Antigen-Promoted Cell Fusion: Antigen-Coated Myeloma Cells Fuse with Antigen-Reactive Spleen Cells" Transplantation Proceedings, vol. XII, No. 3, pp. 443–446, (1980).

Godfrey et al., "Immunospecific Vesicle Targeting Facilitates Microinjection into Lymphocytes" Proceedings of the National Academy of Sciences, 80, pp. 2267–2271 (1983).

Godfrey et al., "Affinity Homing of Sealed Red Cells Ghosts to Cell Surfaces" Federation Proceedings 39(3), p. 719 Abst. #2387 (1980).

Vienken et al., "Electric Field Induced Fusion: Electro-Hydraulic Procedure for Production of Heterokaryon Cells" Febs Letters 137(12) pp. 11–13 (1982).

*Primary Examiner*—John E. Tarcza
*Attorney, Agent, or Firm*—Cushman, Darby & Cushman

[57] ABSTRACT

A process for selectively producing monoclonal antibodies which comprises selectively bringing together proliferating cells and the appropriate B-cells by means of ligand recognition of respective cell surface receptors and then fusing together the proliferating cells and B-cells thus brought together.

2 Claims, 5 Drawing Sheets

Mr
K Dalton
— 45

PREPARATION OF MONOCLONAL ANTIBODIES

The present invention is concerned with the preparation of monoclonal antibodies.

More particularly, the invention provides a process for preparing monoclonal antibodies by selective cell fusion whereby efficiency of the fusion is greatly improved and the yield of desired monoclonal antibodies is significantly increased.

The invention described herein is based on work supported by USPHS grants.

BACKGROUND OF THE INVENTION

The fusion of myeloma cells and B lymphocytes to form hybridomas which produce monoclonal antibodies has been a major advance in recent biomedical research. See *Nature*, 256, 495–497 (1975); *Nature* 266, 550–552 (1977) and *Eur. J. Pharm.* 6, 511–519 (1976). However, the effectiveness of the process has been hampered by a number of disadvantages, particularly its lack of specificity in terms of the cells which are fused. Usually Sendai virus or polyethylene glycol have been used to induce cell fusion but these materials are normally of poor efficiency, the frequency of successful fusion being usually less than $10^{-5}$. Furthermore, the cell fusion obtained by these methods is nonspecific so that all cells are fused at random whether or not the lymphocytes involved are the type that make antibodies to an appropriate antigen. Typically only a small fraction of myeloma-lymphocyte hybridomas produce antibodies of interest. Extensive immunization with large amounts of antigen has been attempted in efforts to improve the yield of monoclonal antibodies. However, this is not a feasible technique when only a small amount of the antigen is available. Additionally, the high frequency of random fusion requires a stringent, extensive and often laborious screening process to separate out and recover the desired monoclonal antibodies.

High voltage electrical fields have also been employed for cell fusion. See, for example, *Sixth Int. Biophys Cong. Kyoto Abstr.* IV-19(H), p. 140 (1978); *Naturwissenschaften* 67, 414–145 (1980); *Current Genetics* 4, 165–166 (1981); and *Science* 216, 537–538 (1982). When used in conjunction with dielectrophoresis to secure cell alignment, quantitative cell fusion can be obtained. See "*Dielectrophoresis*", Cambridge University Press, Cambridge (1978); and *Biochim. Biophys. Acta* 694, 227–277 (1982). Usually a limited number of cells are fused at a time under direct microscopic examination. Direct visualization can distinguish cells with different morphology, but one cannot identify those B-cells destined to secrete the relevant antibodies.

It is also known that B-cells (lymphocytes) express on their surface antigen "receptor" immunoglobulins of the same antigenic specificity as the antibodies secreted therefrom. Antigens are selectively bound to such surface receptors and when so bound stimulate proliferation and differentiation of B-cells into plasma cells, which then secrete antibodies.

GENERAL DESCRIPTION OF THE INVENTION

The invention takes advantage of the selective, high affinity interaction between antigens and specific surface receptor immunoglobulins on B-cells so as to facilitate close adherence of the appropriate B-cells, i.e. those which provide antibodies of interest, and proliferating cells, e.g. myeloma cells, to enable more effective and selective cell fusion with consequent improved efficiency and yield of desired monoclonal antibodies.

More specifically, the invention provides a process for selectively producing monoclonal antibodies effective against a particular antigen by (1) selectively linking together proliferating cells and B-cells which are capable of producing the desired antibodies, the proliferating cells and B-cells being linked together through a linkage which includes antigen bound directly or indirectly to the surface receptors of the B-cells; (2) fusing the thus linked proliferating cells and B-cells to form a hybridoma; (3) cultivating the hybridoma to produce monoclonal antibodies and (4) recovering the resulting antibodies.

The linkage between the proliferating cells and B-cells is preferably formed by attaching a ligand to the surface of the proliferating cells and another ligand attached through the antigen to the surface immunoglobulins or receptors of the B-cells, the respective ligands being so chosen that they selectively recognize and react with each other. Preferably the ligand attached to the proliferating cells, which are advantageously but not necessarily myeloma cells, is biotin and the ligand associated with the antigen is avidin. However, it will be appreciated that other materials can be used in lieu of biotin and avidin as long as they provide the desired recognition and reaction properties. Additionally, the ligands selected must be such that they can be bound to the surfaces of the proliferating cells or selected antigen without destroying the normal function thereof. Thus, for example, the ligand bound to the proliferating cells must not undesirably affect the essential proliferating characteristics of these cells. Likewise the ligand bound to the antigen should not destroy the ability of the antigen to selectively bind to the surface immunoglobulins of the relevant B-cells.

In its broadest aspects, the present process comprises selectively bringing together proliferating cells and the appropriate B-cells by means of ligand recognition of respective cell surface receptors and then fusing the proliferating cells and B-cells thus brought together to form a hybridoma capable of secreting or producing monoclonal antibodies effective against a particular antigen.

In a narrower version, the process involves
(a) combining a first binding component or ligand with a selected antigen to form a binding component-antigen conjugate;
(b) reacting this conjugate with a collection or bulk suspension of B-cells including some capable of forming antibodies effective against the selected antigen whereby the antigen component of the conjugate selectively binds to surface immunoglobulins of the B-cells which provide the desired antibodies;
(c) fixing another binding component or ligand to the surface of proliferating cells, e.g. myeloma cells, the ligands referred to in (a) and (c) being selectively reactable with each other;
(d) combining the reaction product of (b) with the product of (c) whereby the proliferating cells and B-cells bound to the conjugate selectively bind or adhere to each other through their respective ligands;
(e) fusing together the thus selectively adhered proliferating cells and B-cells to form a hybridoma capable of producing monoclonal antibodies effective against the selected antigen;

(f) culturing the hybridoma to form the desired antibodies; and (g) collecting the antibodies thus formed.

Any type of proliferating cell of the tumor or non-tumor types may be used for present purposes although myeloma cells are preferred.

Additionally, a wide variety of antigens may be used, these being selected as desired to provide hybridomas which effectively and usefully secrete antibodies with high affinity. Representative antigens are hereinafter disclosed, i.e. angiotensin converting enzyme, enkephalin convertase and bradykinin, but it will be appreciated that the invention is of broad application in respect of the antigen employed.

Cell fusion is preferably carried out using a high voltage electric field. However, other conventional fusion methods may also be employed to advantage. This includes dimethylsulfoxide, Sendai virus or polyethylene glycol induced cell fusion.

According to one preferred embodiment of the invention, a selected antigen, e.g. enkephalin convertase, is covalently linked to avidin to form an antigen-avidin conjugate. The conjugate is then mixed with a bulk suspension of B-cells whereby the antigen selectively binds to the surface immunoglobulins on the B-cells which provide the appropriate antibodies for the antigen. The resulting B-cell-antigen-avidin complex in bulk suspension is then bound to biotin which has been covalently attached to the surface of myeloma cells or the equivalent. Thereafter the bulk suspension, preferably in diluted form to more or less isolate the selectively bound-together B-cells and myeloma cells from other unbound B-cells, is subjected to cell fusion conditions, preferably by means of an intense electric field, to produce selective fusion of cells in contact, i.e. fusion of myeloma cells with the B-cells which make the appropriate antibody. This results in the formation of hybridomas which secrete appropriate antibodies with high affinity against the initially selected antigen.

It will be appreciated from the foregoing that the invention is based, not only on the selective binding of an antigen to the surface immunoglobulins of only those B-cells which produce the antibody effective against the selected antigen, but also on the provision of recognition sites on the surfaces of the myeloma or like proliferating cells and the appropriate B-cells so that these are selectively and preferentially linked together, i.e. brought into close proximity to each other, notwithstanding the presence of other B-cells which are not relevant to the antigen of concern. These features facilitate the close association of the myeloma or like cells and appropriate B-cells as essential for efficient and selective cell fusion.

Advantageously, as noted earlier, the bulk suspension containing B-cells and myeloma cells or the like is diluted, before cell fusion, in order to separate the linked B-cells and myeloma cells from other irrelevant B-cells. Preferably this dilution is such as to provide a total B-cell concentration of $10^6$ to $10^7$ cells per ml although it will be recognized that other concentrations may be used.

DETAILED DESCRIPTION OF THE INVENTION

Figure 1A:
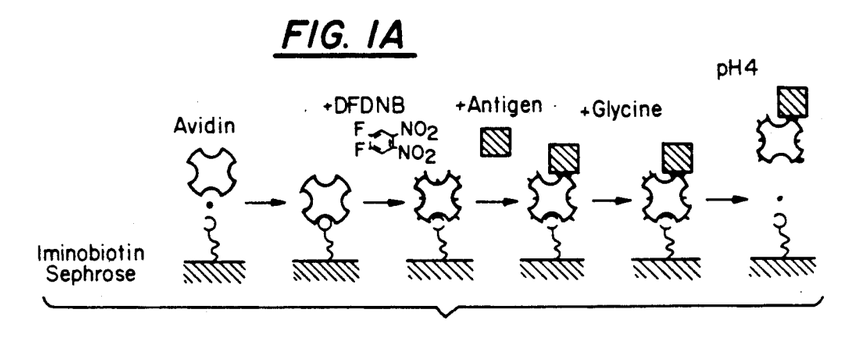
FIG. 1A shows preparation of the antigen-avidin conjugate and FIG. 1B shows biotinylation of myeloma cells and specific adhesion to B-cells.

The invention is illustrated, but not limited, by the following:

(a) Preparation of Antigen-Avidin Conjugate:

Antigen is linked to avidin via a small cross-linking molecule, 1,5-difluoro-2,4-dinitrobenzene (DFDNB). In this procedure it is essential that an adequate amount of antigenic sites be spared to interact with the B-cells. Also, non-productive conjugation between avidin molecules or between antigen molecules must be minimized. Finally, it is necessary to preserve at least one biotin binding site on the avidin molecule. Accordingly, the antigen-avidin conjugate is prepared using an immobilized, reversibly binding analog of biotin, iminobiotin (FIG. 1A). Avidin is mixed with a large excess of iminobiotin coupled to Sepharose in order to minimize avidin-avidin cross-linking. Unbound avidin is then washed away. The bound avidin is reacted with 100-fold excess of DFDNB, which provides a large number of reactive sites on avidin molecules. Following extensive washing to remove unbound DFDNB, antigen is added to the activated avidin bound to iminobiotin Sepharose. Free reactive sites on avidin are blocked with glycine. The antigen-avidin complex is eluted from iminobiotin with a pH 4 buffer. The resulting conjugate or complex has at least one active biotin binding site.

Figure 1B:
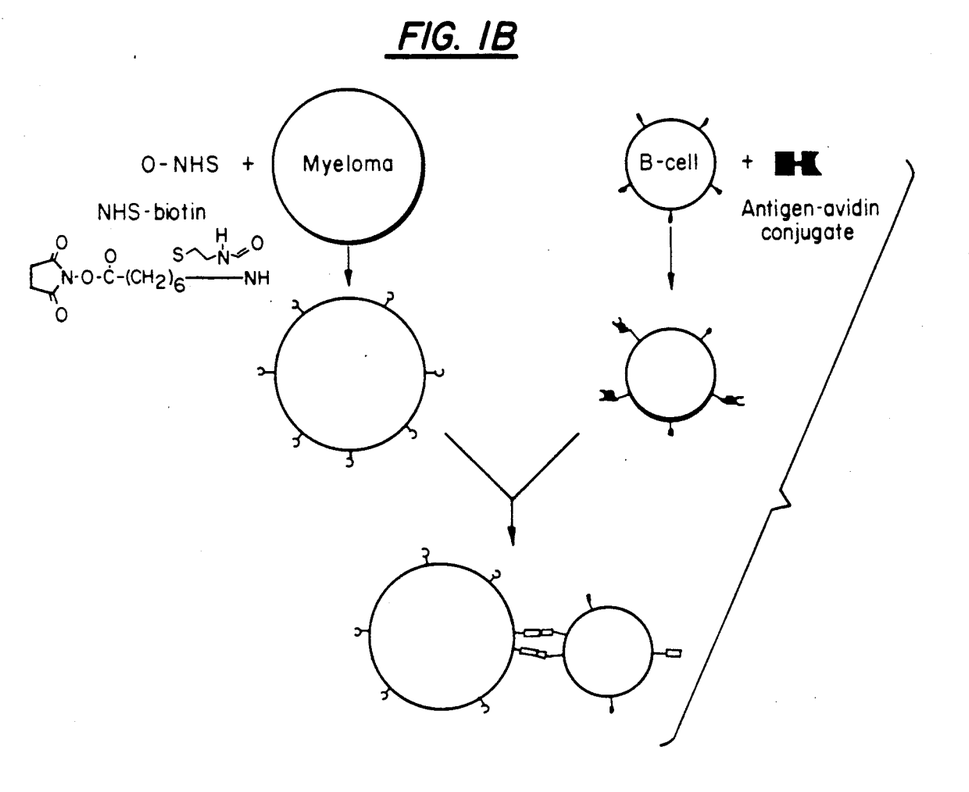

(b) Cell Fusion:

The antigen-avidin conjugate from (a) is reacted with B-cells obtained from mice that have been immunized with the appropriate antigen, i.e. the same antigen as used in (a). This reaction is conducted at 4° C. to prevent capping and internalization of the conjugate. The B-cells are then washed to remove unbound conjugate. Myeloma cells are reacted with an N-hydroxysuccinimide derivative of D-biotin. This procedure is gentle and myeloma cell viability is preserved. The myeloma cells are washed to remove unreacted biotin. The myeloma and B-cells are then incubated together at 4° C. to permit adhesion of the biotinylated myeloma cells with those B-cells having antigen-avidin conjugate bound to their surface immunoglobulins (FIG. 1B). A wide range of cell type ratios can be employed.

The cells are suspended in sucrose and then exposed to a transient electric field generated by a high voltage pulse generator. Isosmotic sucrose is used because of its low electrical conductance. Enough heat is generated by electric fields in isotonic solutions to severely damage cells. The cell suspension is dilute in order to minimize random fusion of cells. Under these conditions the fusion frequency of cells not treated with antigen-avidin conjugate is less than $10^{-8}$. Typically, 0.15 ml of a suspension containing about $10^7$ myeloma cells and $10^7$ B-cells is exposed to four 5 microsecond pulses at 4 KV per cm. The instrument used to fuse the cells is that described by Kinosita et al., *Proc. Nat'l. Acad. Sci. USA*, 74, 1923–1927 (1977) and Tsong, *Bioscience Reports*, 3, 487–505 (1983).

Following fusion, cells are plated at about $10^5$ cells per well into plates seeded with about $10^4$ murine peritoneal macrophages per well. The medium contains aminopterin, which selects for hybrids (see Littlefield, *Science*, 145, 709–710 (1964)). Wells with growing colonies are screened for antibody production.

(c) Hybridoma Screening:

Initially monoclonal antibodies were raised against rat lung angiotensin converting enzyme (ACE). ACE is a dipeptidylcarboxypeptidase (EC 3.4.15.1) which removes a dipeptide from the carboxyl terminal of the 10 amino acid peptide angiotensin I to form an 8 amino acid peptide angiotensin II. Angiotensin II is a potent regulator of blood pressure, stimulates the secretion of aldosterone, the salt retaining hormone, and stimulates drinking behavior. ACE also inactivates the hypotensive peptide bradykinin. These actions of ACE are relevant to blood pressure regulation, since ACE inhibitors such as captopril are clinically useful antihypertensive agents. See Cushman et al., *Biochem. Pharmacol.* 29, 1871-1877 (1980).

Two different immunization procedures were used in separate studies of antibody formation to ACE. In the first study (Fusion A), a C57 BL/6 mouse received an intraperitoneal injection (i.p.) of crude rat lung membranes followed by a second injection four weeks later. After another two weeks, 2 μg of pure rat lung ACE (prepared by a modified method reported in *J. Biol. Chem.* 257, 14128-14133 (1982)) was injected intraperitoneally. Three days later the spleen was removed and the cells were fused as described above.

In a second experiment (Fusion B), a C57 BL/6 mouse received two i.p. injections of pure ACE (2 μg) five days apart. Three days after the second immunization the spleen cells were fused, also as described above.

Figure 2:
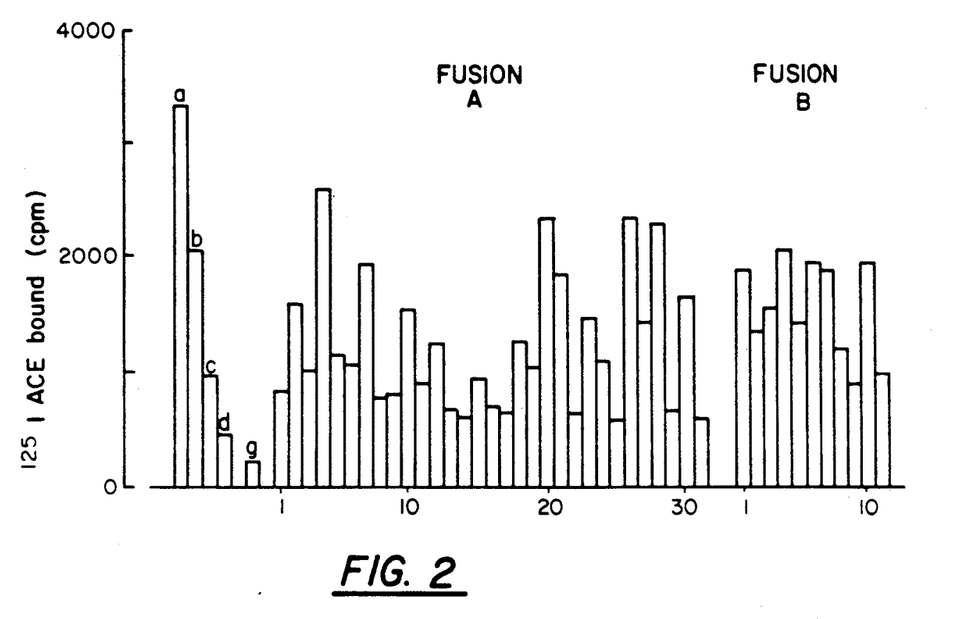
FIG. 2 demonstrates the results of screening for anti-ACE activity.

Half of the cells from Fusion A were plated into 72 wells. A total of 31 wells produced growing hybrids after 6 weeks, and all wells gave evidence of antibody formation against ACE (FIG. 2). Half of the cells from Fusion B were plated into 144 wells. Eleven wells showed cell growth and again all of these wells produced antibodies to ACE (FIG. 2). Examination of growing wells from Fusion A and Fusion B revealed only a single growing colony in each well. The hybridomas were cloned twice by limiting dilution. See *Method in Enzymol.* 73, 1-46 (1981).

(d) Antibody Characterization:

Subclass specific antisera were used to determine the immunoglobulin subtypes of 31 monoclonal antibodies. A spectrum of subtypes was generated: 2 were Igm, one was IgG1, one was IgG3, and the rest were either IgG2a or IgG2b. One antibody had lambda light chains, the remainder reacted with anti-kappa antiserum.

Figure 3:
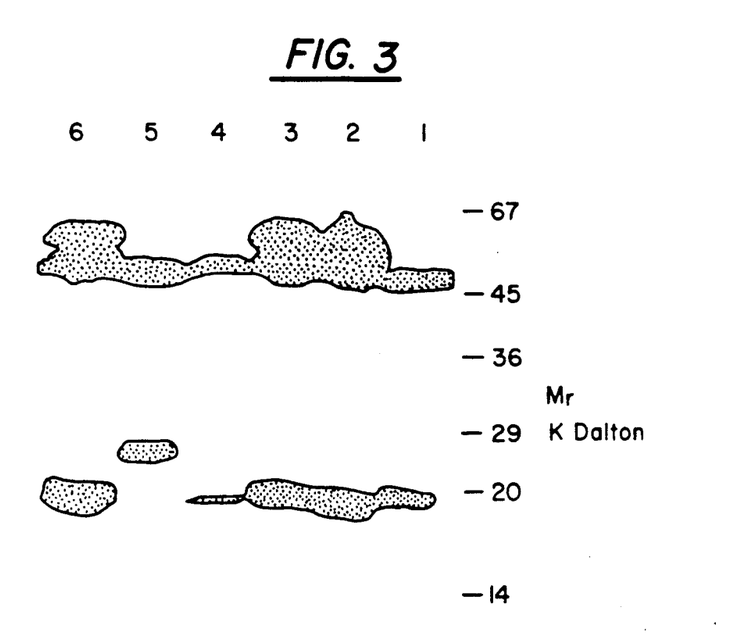
FIG. 3 illustrates the results obtained by polyacrylamide gel electrophoresis of anti-ACE monoclonal antibodies obtained according to the invention.

Gel electrophoresis analysis of six purified monoclonal antibodies revealed in all cases a single light chain of about 20,000-25,000 daltons. For three of the antibodies a doublet was apparent for the heavy chain. These were all of the γ2b subtype (FIG. 3). These results confirm the diversity found in the subclass typing experiments, and indicate that the antibodies examined were not derived from the same B-cell.

Figure 4A:
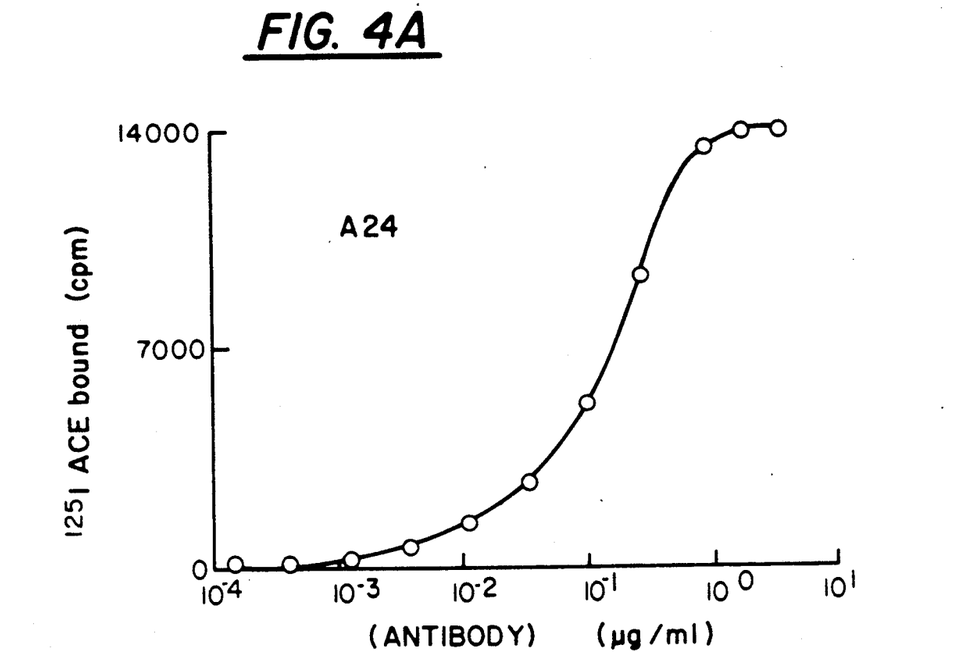
Figure 4B:
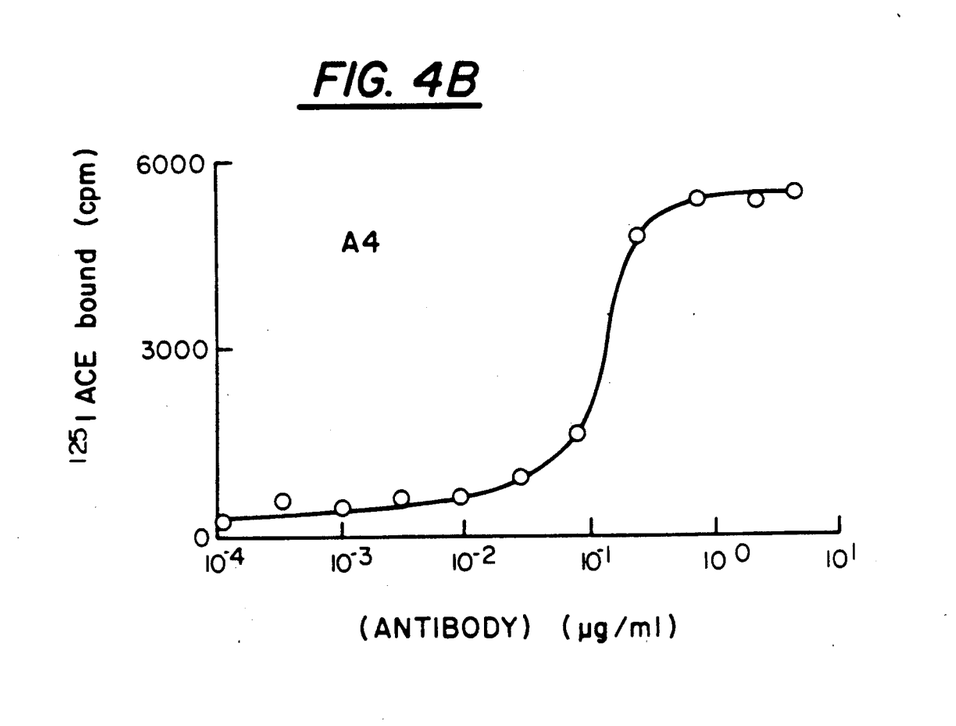

Monoclonal antibodies normally have lower antigen binding affinities than polyclonal antibodies raised against the same antigen. Since fusion of myeloma cells and lymphocytes according to the invention depends on antigen-antibody recognition, hybridomas prepared by the present method should produce high affinity antibodies even with spleen cells obtained during a primary response. Accordingly, the affinities of monoclonal antibodies for ACE prepared as described above have been evaluated and affinities (defined by the concentration of antibody required to bind 50% of added $^{125}$I-ACE) ranged from $10^{-8}$M to $10^{-10}$M (FIG. 4). This high affinity was confirmed in kinetic experiments with antibodies A4 and A24 which associated to $^{125}$I-ACE with half-lives of about 13 minutes and complete association by 30 minutes at 35° C. Dissociation rates were obtained by incubating antibody bound to *Staphylococcus aureus* cells with excess $^{125}$I-ACE to equilibrium, removal of free $^{125}$I-ACE and addition of unlabeled ACE in 1,000-fold excess over bound $^{125}$I-ACE. The half-life for dissociation at 35° C. was about three hours for antibody A24 and about eight hours for antibody A4.

Figure 5:
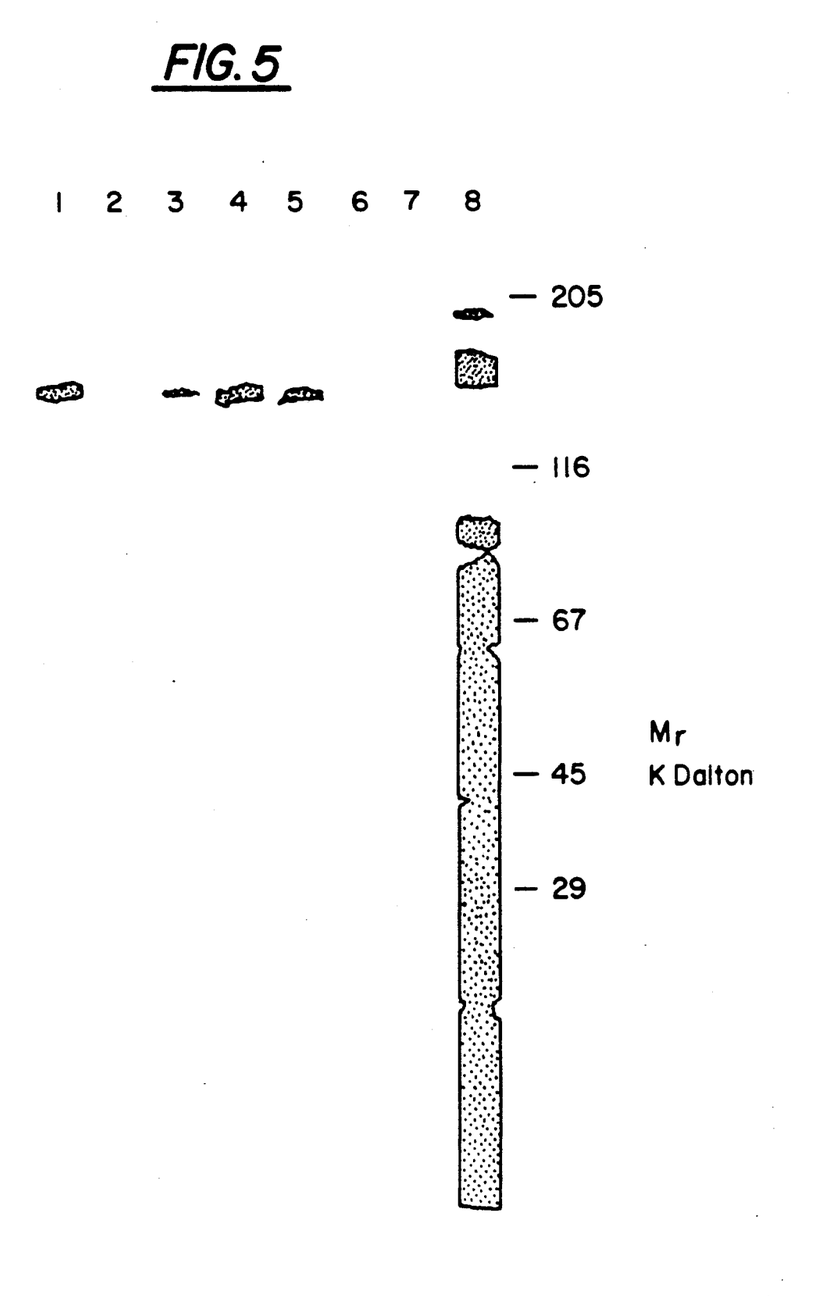
FIG. 5 shows the specificity of monoclonal antibodies obtained by the present invention in terms of staining crude rat lung extract transferred onto a nitrocellulose membrane after SDS polyacrylamide gel electrophoresis.

The specificity of the anti-ACE antibodies was established by a Western blot analysis (FIG. 5). Crude rat lung extract (containing ACE) was subjected to SDS gel electrophoresis and transferred to a nitrocellulose membrane. Strips of the membrane were reacted with the various anti-ACE monoclonal antibodies and then stained with peroxidase conjugated to rabbit anti-mouse antibody. In all cases the anti-ACE antibodies obtained by the present invention reacted with only a single band which corresponded to authentic ACE. Since ACE concentration in the rat lung extract was less than 0.1% of total protein, the test indicates high specificity for the monoclonal antibodies examined.

Figure 6:
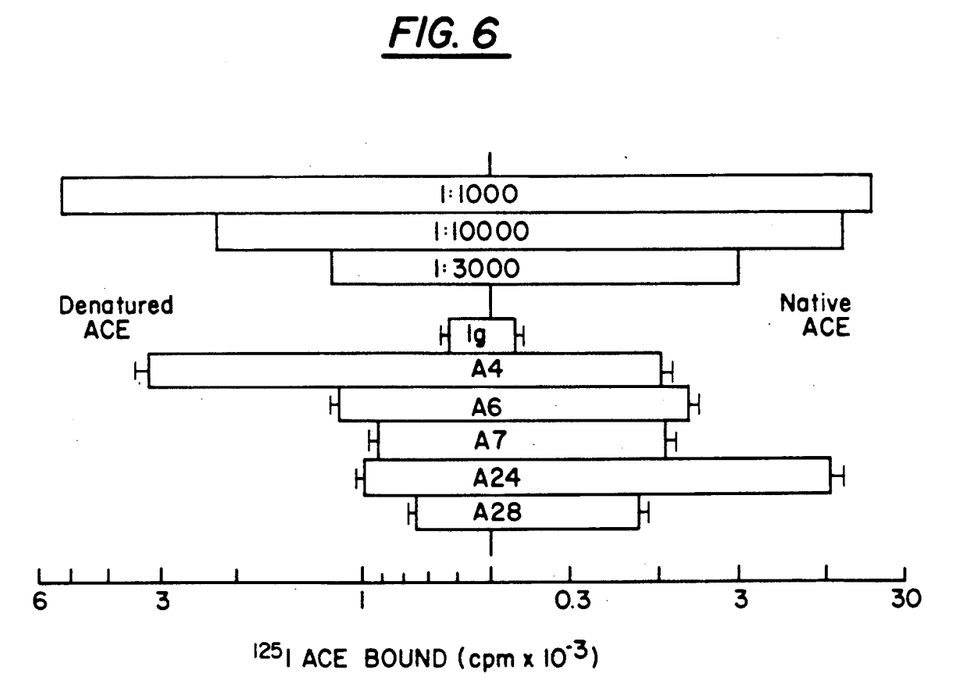
FIG. 6 illustrates the different epitope specificity of the anti-ACE monoclonal antibodies of the invention.

To study the properties of different determinants present on a single antigen, investigators often develop large libraries of monoclonal antibodies. Monoclonal antibodies produced from repeated fusions with animals immunized to a particular antigen, for example, the acetylcholine receptor (*Proc. Natl. Acad. Sci. U.S.A.*, 77, 755-759 (1980)) frequently yield many antibodies directed to a dominant epitope. To examine the epitope specificity of the antibodies obtained by the present invention, their reactivity was compared with native and denatured $^{125}$I-ACE (FIG. 6). For the five monoclonal antibodies evaluated, considerable differences in relative reactivity to denatured and native ACE were observed. This strongly suggests that the antibodies obtained according to the invention recognize different epitopes on the antigen.

(e) Antibodies to Enkephalin Convertase and Bradykinin:

To assess the general applicability of the present method, it has also been used to develop monoclonal antibodies against enkephalin convertase, an enkephalin forming carboxypeptidase (see *J. Biol. Chem.* 258, 10950-10955 (1983)), and against the nine amino acid peptide bradykinin. A mouse received an i.p. injection of 2 μg of enkephalin convertase mixed with complete Freund's adjuvant followed five days later by another injection of 2 μg of enkephalin convertase alone. Three days thereafter its spleen cells were linked to avidin-enkephalin convertase and fused with biotinylated myeloma cells, all as described above. Four wells containing growing cells were obtained out of a total of 72 wells. All four wells had antibody activity against enkephalin convertase, as measured by depletion of soluble enzyme activity with antibody precipitated by *S. aureus* cells.

To develop antibodies to bradykinin, a mouse received an initial injection of 5-20 μg of bradykinin conjugated to human albumin together with complete Freund's adjuvant, followed five days later with an injection of the bradykinin-albumin conjugate alone. Spleen cells were fused three days later using a bradykinin-avidin conjugate. Of seven growing wells (from a total of 120 wells), all demonstrated antibody activity to bradykinin as determined by radioimmunoassay using $^{125}$I-Bolton-Hunter labeled methionyl-lysyl-bradykinin.

Screening of these antibodies involved immunoprecipitation by *S. aureus* cells at 35° C., in filtration or centrifugation assays. Under these conditions, immunocomplexes with affinities that are weaker than $K_D = 10^{-8}M$ dissociate too rapidly for detection. Similar methods have been widely used to study ligand binding to neurotransmitter receptors, and in these experiments, also, complexes with $K_D$ values greater than $10^{-8}M$ are not detectable; see, *Science*, 224, 22-31 (1984). This indicates that the anti-bradykinin and anti-enkephalin convertase antibodies have high affinity for the antigens, with dissociation constants apparently less than $10^{-8}M$.

To confirm that hybridomas formed by the present method result from antigen-antibody recognition, the following experiment was performed:

A pure F (ab')$_2$ fragment of sheep antibody raised against mouse IgM and IgG was covalently conjugated to avidin and used to elicit fusion between biotinylated myeloma cells and mouse spleen cells. One percent of the spleen cells fused with myeloma cells and survived HAT selection, and most of these resultant hybridomas secreted mouse IgG.

As noted, it is preferred to use a high voltage electric field for cell fusion according to the invention since this seems to give the best results. Significantly, previous efforts using electric field induced cell fusion together with pronase treatment of cells and dielectrophoresis to promote adhesion prior to fusion, have not been particularly successful in producing monoclonal antibodies. See, for example, *FEBS Lett.*, 137, 11-13 (1982). In experiments preliminary to the present invention, cells were treated with concanavalin A or pronase to elicit cell adhesion. It was possible in this way to obtain fusion frequencies of $10^{-1}$-$10^{-2}$, which is four to five orders of magnitude greater than the efficiency of cell fusion obtained with polyethylene glycol. Furthermore, most of the hybridomas produced in this way secreted mouse immunoglobulins. Thus, cell suspensions subjected to high voltage fields can provide very large numbers of fused cells. However, for the production of monoclonal antibodies, the resultant millions of growing colonies pose a vast problem for screening. Accordingly, in the present method, the frequency of cell fusion has been reduced by diluting the cell suspensions and by avoiding agents which promote non-specific cell adhesion. Instead, advantage is taken of antigen-antibody recognition as a means to select a small number of heterokaryons which secrete antibodies with high affinity for the enzymes ACE and enkephalin convertase and the peptide bradykinin. The results obtained confirm the feasibility of the present method and indicate its general applicability.

The method of the invention provides a number of advantages over existing procedures. For one thing, very small amounts of antigen can be used. In conventional techniques for producing monoclonal antibodies, hyperimmunization with large amounts of antigen is usually attempted prior to fusion, in order to elicit a secondary response with antibodies of reasonably high affinity. By contrast, the present method provides high affinity antibodies of mainly the IgG type from a primary response after immunization with minute quantities of antigen. This apparently occurs because of the selection by the avidin-antigen conjugate or equivalent of those few high affinity immunoglobulin secreting cells which are stimulated to proliferate during a primary response. The specificity of this cell fusion technique provides a great reduction in the number of growing hybridomas that must be screened for antibody production. Furthermore, with the present procedure, using the appropriate antigen-avidin conjugate or the like, all hybridomas formed produce desired antibodies.

The cell fusion method described herein, based on high affinity cell specific recognition, is believed to have other applications besides the indicated antigen-antibody interactions. Thus, the method can be used for drug, hormone or neurotransmitter recognition by receptor sites as a selection tool. Accordingly, with liposomes or red cell ghosts as one of the fusing elements, it is possible to deliver to various cells the contents of the liposome or ghosts, such as genes, proteins, or drugs. For example, selected genes contained in biotinylated liposomes can be introduced into nerve cells with specific surface receptors that have been labeled with drug-avidin complexes.

DESCRIPTION OF THE DRAWINGS

The accompanying drawings illustrate various aspects of the invention as follows:

FIG. 1 diagrammatically illustrates in Schemes A and B the method for obtaining specific cell-cell adhesion according to the invention.

FIG. 4 is a graph showing the results obtained in the titration of $^{125}$I-ACE with anti-ACE antibodies prepared according to the invention to illustrate the ACE affinity of two antibodies, FIG. 4A pertains to monoclonal antibody A24 and FIG. 4B pertains to monoclonal antibody A4;

DETAILED DESCRIPTION OF THE INVENTION

The invention is described in more detail by the following examples:

EXAMPLE 1

Preparation of Antigen-Avidin Conjugate

Using the reaction scheme illustrated in FIG. 1A, iminobiotin-Sepharose (0.1 ml gel containing 1 μmole iminobiotin), previously reacted with 1,5-difluoro-2,4-dinitrobenzene (DFDNB) and glycine, is incubated with avidin (10 μmoles for 2 hr at 20° C. The resin is washed with 10 ml 0.1M Na borate buffer (pH 8.5) and 1 μmoles of DFDNB dissolved in 10 μl methanol, then washed off after 10 min. at 20° C. Pure antigen (1 μg) is reacted with the activated immobilized avidin for 12 hr at 4° C. After removal of unbound antigen, glycine (0.1 μmole) is added to block the remaining reactive sites. The antigen-avidin conjugate is eluted from the resin with 0.2 ml 50 mM citratephosphate (pH 4).

EXAMPLE 2

Biotinylation of Myeloma Cells and Specific Adhesion to B-Cells

Referring to the reaction scheme shown in FIG. 1B, $10^7$–$10^8$ myeloma cells (P3×63Ag8.653) were washed with phosphate buffered saline, resuspended in 5 ml buffered saline and incubated with N-hydroxysuccinimide (NHS) linked to biotin ($5\times10^{-7}$ moles dissolved in 50 µl dimethylformamide) for one hour at 4° C. Cells were extensively washed with cold Dulbecco's modified Eagle's medium (DMEM) containing deoxyribonuclease I (DNase) (50 µg/ml) to remove unbound biotin. Spleen cells from an immunized mouse were incubated with the antigen-avidin conjugate in 5 ml DMEM for four hours at 4° C. Spleen cells were washed with cold DMEM containing DNase to remove excess conjugate, mixed with biotinylated myeloma cells and centrifuged at 200×g for five minutes. The pellet was then incubated for three hours at 4° C. and washed with DMEM containing biotin ($10^{-6}$ moles/ml) and DNase. The cells were finally resuspended in isosmotic sucrose and fused by four exposures to 4 KV/cm for 5 microseconds at 30° C.

EXAMPLE 3

Screening for Anti-ACE Activity

Supernatants (0.2 ml) from wells with growing hybridomas (31 from Fusion A and 11 from Fusion B) were incubated with $^{125}$I-ACE (2 pg consisting of about 50,000 cpm) in buffer containing 50 mM Tris HCl, 0.2M NaCl, 0.1% (w/v) Triton X-100 (pH 7.7) for two hours at 35° C. Rabbit anti-mouse IgG (2 µg) was added and incubated for one hour at 37° C. followed by addition of S. aureus cells (2.5 mg) and incubation for one hour at 37° C. The suspension was poured over Whatman GF/B filters, washed with 10 ml of buffer, and bound radio-activity determined. Positive controls consisted of a goat antiserum (Biochemistry, 15, 5088–5094 (1976), raised against ACE and diluted as follows into normal goat serum: 3,000 (a), 10,000 (b), 30,000 (c), and 100,000 (d). Negative controls were normal mouse serum diluted from 1,000–100,000 (not shown) and a mouse IgG2a monoclonal antibody produced against a toxin from Russell viper venom (g). In either case, the amount of bound radioactivity was typically 300 cpm with less than 5% standard deviation.

Colonies developed between fifteen days to four weeks after the fusion. The data shown in FIG. 2 represents the anti-ACE activity in confluent wells. After eight weeks, all wells containing growing cells, when assayed with 10 pg of $^{125}$I-ACE, had antibody activities at least 5-fold greater than the negative control. Some clones had longer doubling times, up to 20–30 hours. However, antibody concentrations were usually 1–5 µg/ml when cells were confluent.

EXAMPLE 4

This example, together with FIG. 3, illustrates polyacrylamide gel electrophoresis of anti-ACE monoclonal antibodies and the results obtained thereby.

Cloned hybridomas obtained as described in the foregoing examples were grown in serum-free HB101 medium and purified over Protein A-Sepharose as described in Method in Enzymol., 73, 1–46 (1981). Samples boiled in SDS and β-mercaptoethanol were electrophoresed on a 12.5% polyacrylamide gel (Nature, 227, 680–685, 1970), and stained with silver (Science, 211, 1437–1438, 1980). Monoclonal antibodies shown in lanes 1–6 are designated A4, A6, A23, A26 and A28, respectively, of FIG. 3.

EXAMPLE 5

Titration of $^{125}$I-ACE with Anti-ACE Antibodies

Hybridomas were grown in serum-free HB101 medium and purified on Protein A-Sepharose as described in Example 4. Protein concentrations were determined as described in J. Biol. Chem. 193, 265–275 (1951). Monoclonal antibody A24 was diluted in 50 mM Tris HCl (pH 7.7) containing 0.2M NaCl, 0.1% Triton X-100 and 10% (v/v) calf serum and incubated with $^{125}$I-ACE (80,000 cpm) in a total volume of 0.25 ml. The final concentration of $^{125}$I-ACE was about $10^{-15}$M. The amount of $^{125}$I-ACE bound to antibody precipitated with S. aureus cells was determined as described in Example 3. A similar procedure was used with monoclonal antibody A4 except that denatured $^{125}$I-ACE was employed. Pure ACE was denatured by treatment at 100° C. for five minutes in 1% SDS and 5% β-mercaptoethanol prior to iodination and gel filtration. The concentrations of A24 and A4 required to bind 50% of the total amount of precipitatable $^{125}$I-ACE are 1 nM and 0.8 nM, respectively. The ordinate in FIG. 4 is the specific bound $^{125}$I-ACE. The nonspecific binding is typically 300 cpm.

EXAMPLE 6

This example illustrates, together with FIG. 5, the specificity of monoclonal antibodies staining crude rat lung extract transferred onto a nitrocellulose membrane after SDS polyacrylamide gel electrophoresis.

Rat lungs were homogenized, extracted (5 ml/g) with 50 mM Tris HCl, 0.2M NaCl and 1% (w/v) 3-[(3-cholamidopropyl)-dimethylammonio]-1-propane-sulfonate (CHAPS) (pH 7.7), and dialyzed to remove the detergent. The extract was electrophoresed on a 7.5% polyacrylamide gel, then electrophoretically transferred to a nitrocellulose membrane which was incubated with 20% calf serum for one hour at 20° C., and cut into strips. The strips were incubated for four hours at 20° C. with purified antibodies from 6 cloned hybridomas - A4, A6, A23, A24, A26, and A28 (lanes 1–6, respectively of FIG. 5) and washed 3 times with 20 mM Tris HCl, 0.2M NaCl and 0.1% (v/v) Tween-20 (pH 7.7). A second antibody linked to peroxidase was used to visualize mouse antibody bound to the strips. A negative control (lane 7, FIG. 5) was a mouse IgG2a monoclonal antibody raised against a toxin in Russell viper venom. The total protein present is demonstrated with a strip (lane 8 of FIG. 5) not incubated in serum but stained with 0.02% amido-black in methanol:acetic acid:water (50:10:40).

EXAMPLE 7

This example, in conjunction with FIG. 6, shows that anti-ACE monoclonal antibodies obtained as in Example 2 above have different epitope specificity.

Five monoclonal antibodies obtained as described were compared by binding equal amounts of the same antibodies to native or denatured $^{125}$I-ACE using the assay described in Example 5. The negative control consisted of a mouse monoclonal IgG2a as described in Example 3. As shown in FIG. 6, each monoclonal antibody shows preferential binding to one or the other form of the antigen in contrast to the anti-ACE goat antiserum diluted from 1,000 to 30,000 times. Note the log scale of the abscissa in FIG. 6.

Various modifications may be made in the invention as described and exemplified above. It will be appreciated that the invention broadly contempaltes using biochemical reagents to create selective recognition by and between myeloma or like cells and B-cells which make the appropriate antibody, with resultant adhesion to facilitate cell fusion. As an alternative to the avidin-biotin linkage described in the foregoing, an appropriate antibody could be bound to the surface of the myeloma cells for selective binding to antigen bound to the surface of the B-cells. Preferably, the avidin/biotin linkage is used but it is possible, as indicated, to omit this linkage in favor of an antibody, receptor or other type of ligand which will direct the myeloma cells to the target B-cells. Other alternative chemical binding means which may be used for this purpose include proteins such as lactins or hydrazines, chemical linkages such as sulfur bonds, etc. provided these do not cause interfering reactions to occur.

B-cells for use herein may be obtained from any convenient source. The foregoing description utilizes the B-cells obtained from the spleens of mice which have been immunized against specific antigens. However, B-cells can be obtained from any animal including man, and may be immunized *in vivo* or *in vitro*.

Various other modifications are contemplated. Accordingly, the scope of the invention is defined in the following claims wherein:

We claim:

1. A process for selectively producing monoclonal antibodies which bind to a particular antigen which comprises
   (a) combining a first binding component with the antigen to form a binding component-antigen conjugate;
   (b) reacting the conjugate obtained in (a) with a collection of B-cells including some capable of forming antibodies which bind to said antigen whereby the antigen component of the conjugate selectively binds to surface immunoglobulins of the B-cells which provide said antibodies;
   (c) binding a second binding component to the surface of myeloma cells, said first and second binding components being selectively reactable with each other;
   (d) combining the reaction product of (b) with the product of (c) whereby the myeloma cells and B-cells bound to said conjugate selectively bind or adhere to each other through said first and second binding components and the antigen;
   (e) fusing together the thus selectively adhered myeloma cells and B-cells by means of a high voltage electric field to form a hybridoma capable of producing monoclonal antibodies which bind to said antigen;
   (f) culturing said hybridoma to form said antibodies; and
   (g) collecting the antibodies thus formed.

2. A process according to claim 2 which comprises linking a selected antigen to avidin, so as to form an antigen-avidin conjugate, mixing the resulting conjugate with B-cells whereby the antigen of the conjugate selectively binds to the surface immunoglobulins of those B-cells which provide the appropriate antibodies for said antigen, providing myeloma cells with a biotin linkage, thereafter incubating the myeloma cells and B-cells together to permit adhesion of the biotinylated myeloma cells and B-cells having the antigen-avidin conjugate by reaction between the biotin and avidin to form a B-cell-antigen-avidin-biotin-myeloma cell complex, fusing the thus bound B-cells and myeloma cells to each other by means of a high voltage electric field to provide a hybridoma which secretes monoclonal antibodies which bind to said antigen, cultivating said hybridoma to form said monoclonal antibodies and recovering the monoclonal antibodies thus formed.

* * * * *